United States Patent [19]

Krol

[11] Patent Number: 4,791,371

[45] Date of Patent: Dec. 13, 1988

[54] APPARATUS USEFUL IN MAGNETIC RESONANCE IMAGING

[75] Inventor: George S. Krol, Mamaroneck, N.Y.

[73] Assignee: Memorial Hospital for Cancer and Allied Diseases, New York, N.Y.

[21] Appl. No.: 931,613

[22] Filed: Nov. 17, 1986

[51] Int. Cl.[4] ............................................. G01R 33/20
[52] U.S. Cl. .................................... 324/318; 128/653
[58] Field of Search ............... 324/300, 307, 312, 309, 324/318, 322; 128/653

[56] References Cited

U.S. PATENT DOCUMENTS

| | | | |
|---|---|---|---|
| 3,789,832 | 2/1974 | Damadian | 324/309 |
| 4,339,716 | 7/1982 | Young | 324/309 |
| 4,411,270 | 10/1983 | Damadian | 324/309 |
| 4,629,989 | 12/1986 | Riehl | 324/318 |
| 4,634,980 | 1/1987 | Misic | 324/322 |
| 4,638,252 | 1/1987 | Bradshaw | 324/318 |
| 4,652,826 | 3/1987 | Yamamoto | 324/318 |

Primary Examiner—Michael J. Tokar
Attorney, Agent, or Firm—John P. White

[57] ABSTRACT

Apparatus are described which is useful in continuous operation of magnetic resonance imaging studies. The apparatus permits examination of subjects without repositioning of the subject and produces more accurate studies than previously possible.

5 Claims, 3 Drawing Sheets

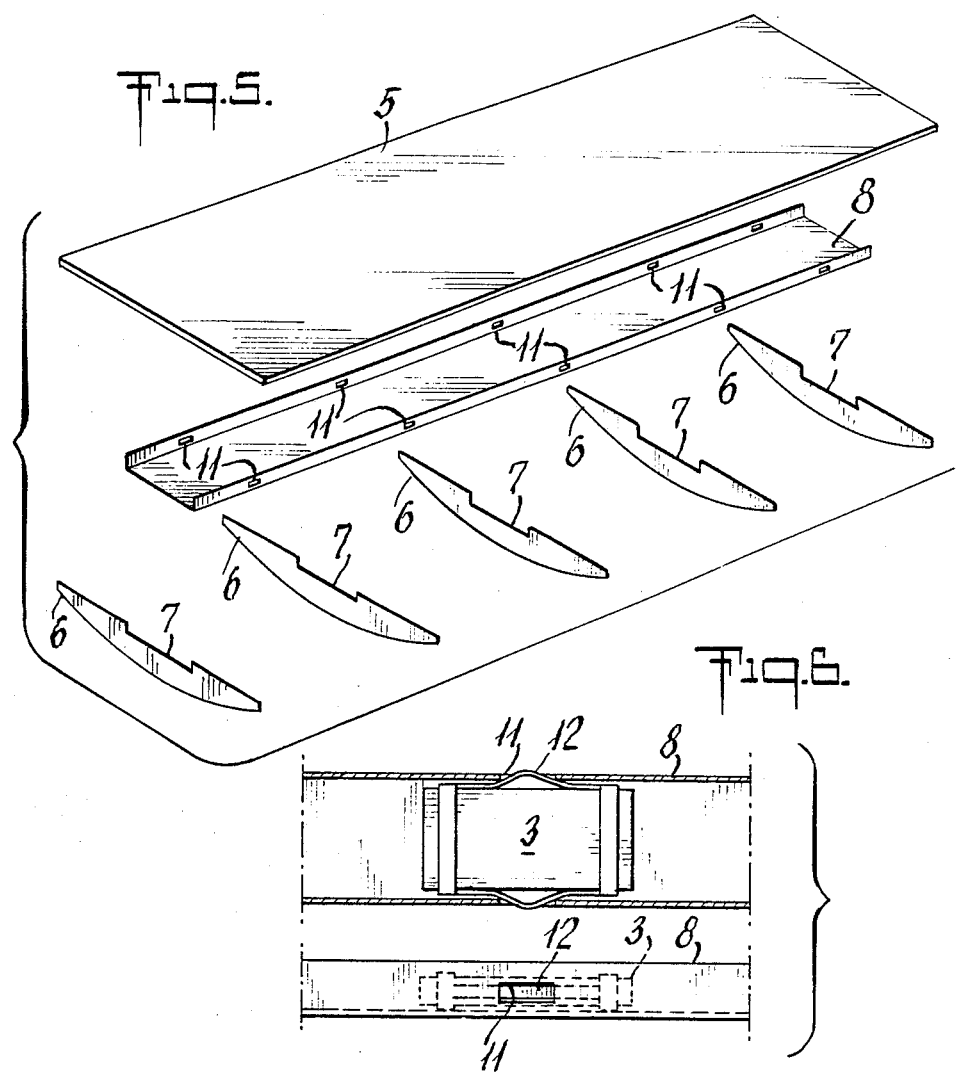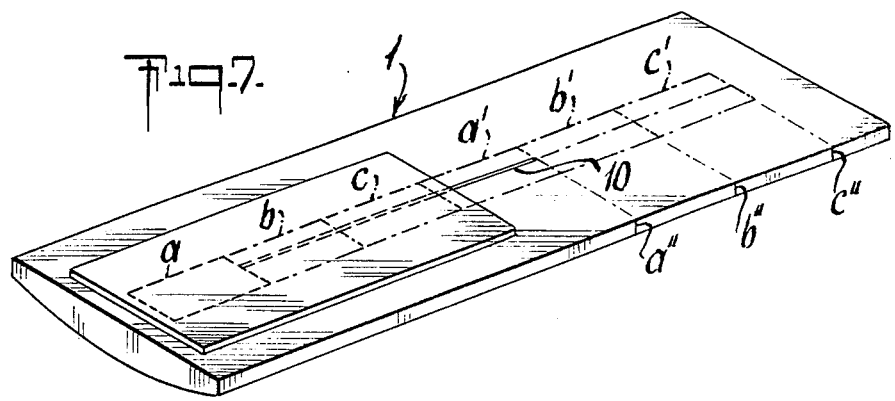

APPARATUS USEFUL IN MAGNETIC RESONANCE IMAGING

FIELD OF THE INVENTION

This invention relates to apparatus useful in the Magnetic Resonance Imaging (MRI). More specifically it relates to an apparatus which permits total or extended MRI examination of a subject without the need to reposition the subject during a series of imagings.

BACKGROUND OF THE INVENTION

Magnetic Resonance Imaging (MRI) is a recently developed method of evaluation of a subject, such as a human. Anatomical and tissue characterization of the human body are examples of applications of the technique.

In a very broad sense one may compare MRI to standard imaging technologies, such as X-ray and CT scanning. On a fundamental level, however, there is no meaningful comparison, as the basis for each technique is very different. X-ray and CT scanning technologies are well known and will not be summarized here. MRI, briefly, employs the rate of relaxation times of induced magnetization to produce sectional imaging. Many of the risks involved with the use of X-rays, e.g., are not present with the use of MRI, and it can and is used to study all parts of the body.

Of particular interest in the scope of this invention is the examination of longer body parts, such as the spine. In efforts to obtain the best anatomical detail possible, examination using MRI is generally carried out using a solenoid device known as a surface coil. Such devices allow viewing of a particular region of the body, usually not more than 15–25 cm in length. This is much less than the length of the spine, e.g., which is usually between 60 and 100 cm in length. In order to do a complete "sectioning" of a body part such as the spine, the surface coil, which is placed on the examination table upon which the patient rests, must be repositioned at least twice. The repositioning results in increased examination time and patient discomfort. The study obtained may be of inferior quality, since it is quite difficult to reposition the surface coil accurately and "skip overs" may result.

Prior art has all been directed to different, imaging systems, such as X-rays. U.S. Pat. No. 4,232,277 teaches a longitudinal transport carriage which is adapted for use with X-ray film cassettes. The carriage is movable along the length of the patient support platform, and a cassette draw is inserted therein. Clamping jaws then support mount the cassette.

This invention differs from the invention disclosed herein in several respects. First, the patent teaches that cassettes must be inserted and removed. As has been pointed out above, this step almost guarantees that some inaccuracies will result during a series of scans. Continuous examination is not possible. Also, the patent is directed solely to X-rays, which use film, rather than MRI, which uses a surface coil. Finally, as is clear from the patent, the thrust is toward an automatic collimation means, and means for exchange of cassettes via lateral routing.

Additional examples may be found in the patent literature of devices which are used in various X-ray systems, but none of these teach or suggest the present invention. For example, U.S. Pat. No. 4,114,039 teaches an apparatus which is useful in reducing the distance between the patient support table and the roentgenographic device. U.S. Pat. No. 4,196,351 teaches the use of probes in a radiographic detection device which are used to permit different detector placements. Finally, U.S. Pat. No. 3,974,388, teaches a patient support which allows movement of the patient relative to a radiographic apparatus used in preparing sections of a skull.

It will be seen that none of these patents teach or suggest MRI or coil displacement, the major features of this invention.

SUMMARY OF THE INVENTION

The invention provides a device for faster and more accurate MRI study of a patient, which can be used with the majority of existing table support systems, without repositioning of patients, and which can operate safely in a magnetic field environment.

Understanding of the invention will be facilitated by review of the materials which now follow.

BRIEF DESCRIPTION OF THE FIGURES

FIG. 5 is an exploded view of the surface coil housing components.

FIG. 6 shows, in detail, the locking mechanism of the housing.

FIG. 7 shows one example of repositioning of the coil during operation.

DETAILED DESCRIPTION OF PREFERRED EMBODIMENTS

Figure 1:
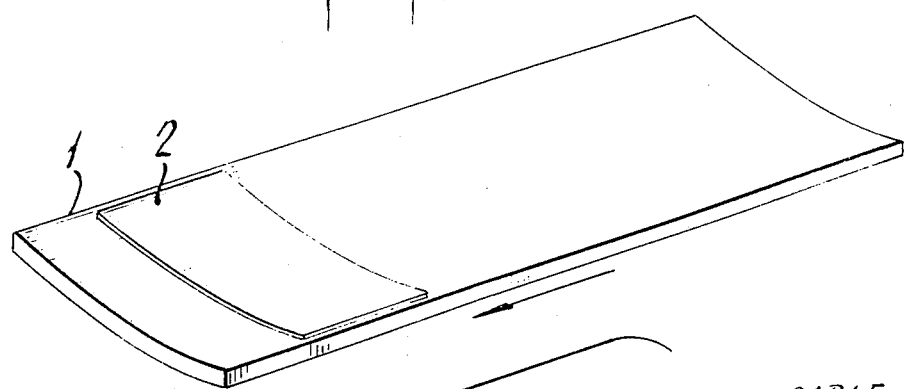
FIG. 1 shows a side-front end view of a typical examination table.
Figure 2:
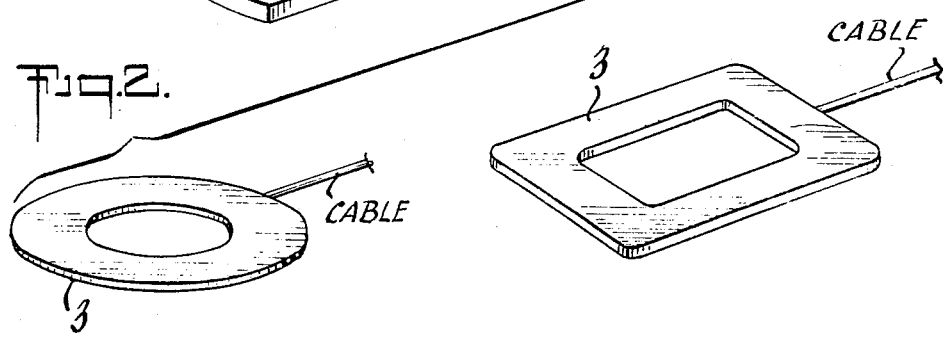
FIG. 2 shows a commonly used surface coil in two embodiments.
Figure 3:
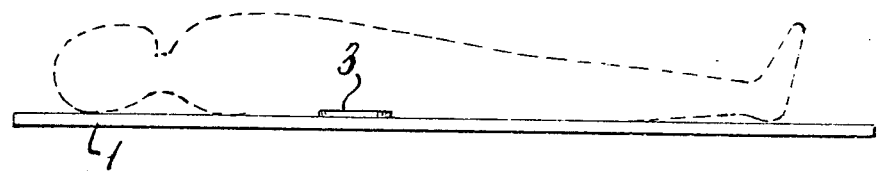
FIG. 3 depicts a side view of a patient during examination of the lumo-sacral region of the spine using MRI surface coil.

As will be noted from FIG. 1, during MRI study a patient is disposed on an examination table (1). A surface coil (3) as shown in FIG. 3, is placed under the patient, beneath the region of interest. This is depicted in FIG. 3 which, for ease of study, does not display the housing for the coil. It must be understood that the coil does not contact the patient. The coil (31) may have a ring shape, a rectangular shape, or other embodiments, which are a matter of design choice.

Figure 4:
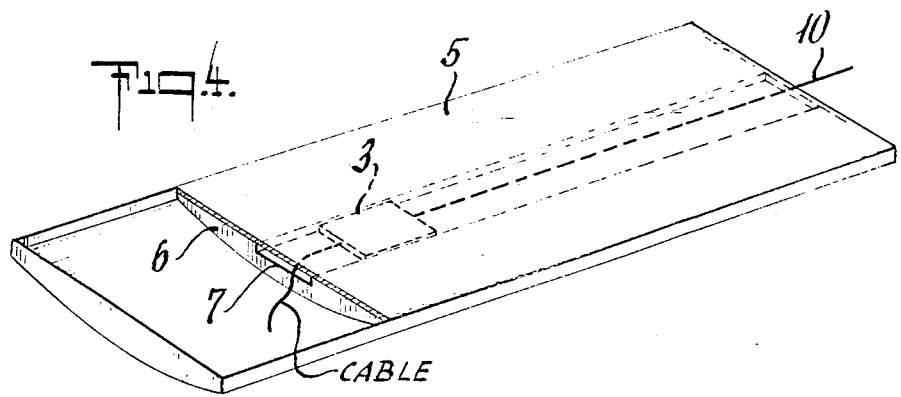
FIG. 4 is a side and front end diagram of the table top, surface coil housing, and surface coil.

In FIGS. 4 and 5, the apparatus is shown in greater detail. A rectangular plate (5) supports the patient. This may be constructed, for example, from plexiglass, wood, or any other rigid, nonmagnetic material. Examples of typical measurements used in construction of the plate are 90 cm (length), 40 cm (width), and 1–1.5 cm thickness.

Semilunar pilars (6), with outer contours fitting the table top (1) are affixed permanently to the plate at equal distances. A rectangular aperture (7), open on its superior side is made in the center of each pilar in order to accommodate a rectangular sleeve, preferably made of plexiglass (8). The sleeve includes openings (11), which operate as locking means when the surface coil is inserted into the sleeve. The openings are spaced equally and in pairs. In one embodiment of the invention three equidistant pairs are used.

The pilars (6), plate (5), and sleeve (8), are all affixed to each other using non ferromagnetic materials so as to minimize interference with the operation of the MRI.

In operation, the surface coil (3), is equipped with a plastic rod (10), which is attached to the rear end of the coil. This is used for positioning the coil in the sleeve. Additionally, the coil is equipped with locking devices (12), which are adapted to fit into the openings (11) in the sleeve such that displacement as a result of, e.g., vibrations, cannot occur.

The sleeve dimensions are chosen such that the coil fits loosely therein and locks in the openings (11), following positioning using the rod means (10). The coil is positioned in the sleeve (8), and is locked into one position. After MRI study of one position is completed, traction of the rod (10), is sufficient to release the coil and to advance it to the next position. Study of the particular region under consideration therefore can proceed without interruption or patient disruption.

Although the locking parts (11) are supported as means of stabilization of the coil in proper position on the longitudinal axis, this also may be done by reference to the longitudinal motion of the rod (10) to the stationary top of the examination table (1). As shown in FIG. 7, the positions of the coil—(a b c) are related to those of the tip of the rod (10)—a'b'c' and marks on the stationary table (1)—a"b"c". The amount of longitudinal travel of the coil depends on its length, generally being equal to it or slightly less.

While the drawings used herein show examination of a spine, one skilled in the art will recognize that this is not the only application of the device. Any body region requiring multiple "scans" to perform a complete study can be so examined. Additionally, one may use the device even where only a single step of examination is required.

The dimensions and form of the embodiment described in this invention device are such as to accommodate one type of surface coil, having the shape of a rectangular plate and known as a "License plate". With minor modifications, the device may be applied to any type surface coils (with exception of wrap-around type) or table top. Also included within the scope of this invention are embodiments wherein the device is built directly into the examination table.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

I claim:

1. Apparatus for examination of a subject using magnetic resonance imaging, comprising:
    (a) a support means for said subject, said support means including non-magnetic plate;
    (b) a plurality of non-magnetic support pilars, said pilars being attached to said plate by non-magnetic means, and adapted for reception of a sleeve means;
    (c) a sleeve means which engages said pilars, said sleeve means comprising a locking means;
    (d) a surface coil for use in magnetic resonance imaging, said coil comprising a second locking means adapted for engagement with the locking means of said sleeve means and said sleeve means and surface coil being so adapted so that said coil fits into said sleeve means and may be moved along the longitudinal axis of said sleeve means; and
    (e) a non-magnetic traction means attached to said coil for moving said coil in said sleeve means.

2. Apparatus of claim 1, wherein said sleeve means comprises a plurality of paired locking means, said locking means equidistantly spaced from each other.

3. Apparatus of claim 1, wherein said surface coil is rectangular.

4. Apparatus of claim 1, wherein said surface coil is ring-shaped.

5. An apparatus of claim 1, wherein the non-magnetic traction means comprises a rod.

* * * * *